United States Patent [19]

Tenny

[11] Patent Number: 4,729,392

[45] Date of Patent: Mar. 8, 1988

[54] DENTAL FLOSS HOLDER

[75] Inventor: Dale E. Tenny, Sunnyvale, Calif.

[73] Assignee: Home Health & Safety, Sunnyvale, Calif.

[21] Appl. No.: 863,301

[22] Filed: May 15, 1986

[51] Int. Cl.⁴ .............................................. A61C 15/00
[52] U.S. Cl. ........................................ 132/91; 132/93
[58] Field of Search .............. 132/89, 91, 92 R, 92 A, 132/93; D28/64

[56] References Cited

U.S. PATENT DOCUMENTS

| D. 250,214 | 11/1978 | Chodorow | D28/64 |
|---|---|---|---|
| 2,354,454 | 7/1944 | Geffner | 132/91 |
| 3,621,853 | 11/1971 | Montalbo | 132/89 |
| 3,642,011 | 2/1972 | Thompson | 132/91 |
| 3,834,404 | 9/1974 | Chien | 132/91 |
| 3,871,392 | 3/1975 | Thomas | 132/89 |
| 4,427,018 | 1/1984 | Lagace | 132/91 |
| 4,434,806 | 3/1984 | Givens | 132/91 |
| 4,460,002 | 7/1984 | Burdette, Jr. | 132/91 |

Primary Examiner—John J. Wilson
Assistant Examiner—Adriene J. Lepiane

[57] ABSTRACT

An improved dental floss holder having a comparatively inflexible elongate member supporting two flexible spaced arms at the opposing ends, and supporting an inflexible spaced arm between. A single length of commercially available dental floss is fastened near the terminal end of either flexible arm, then wrapped around the inflexible spaced arm, then fastened at the flexible spaced arm at the opposite end; two taut and usable lengths of dental floss are thus defined, either of which may be used for flossing while the other end of the dental floss holder is used as a handle. The dental floss fastening systems of the invention include buttons/protrusions in combination with frictional securing slots.

7 Claims, 11 Drawing Figures

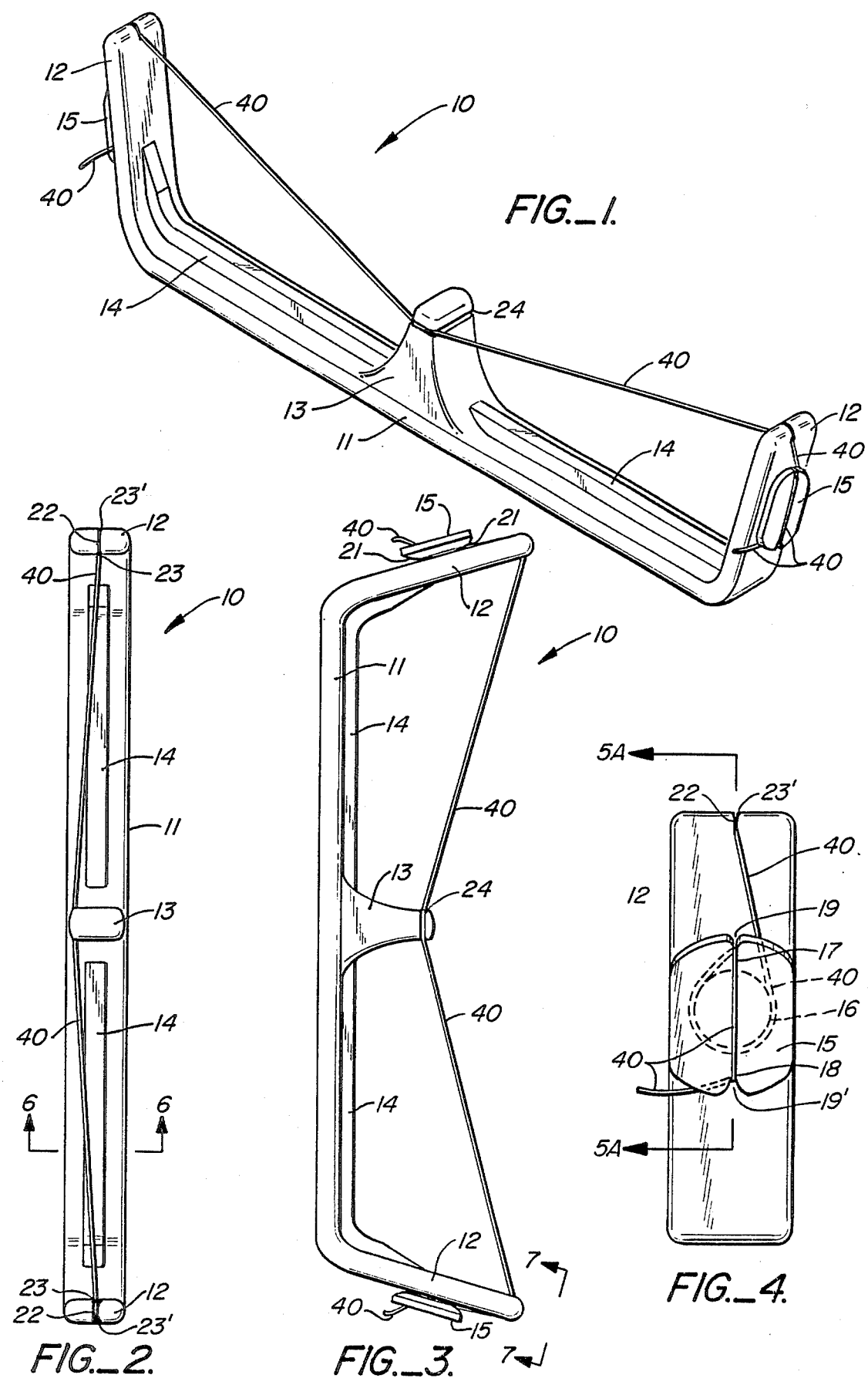

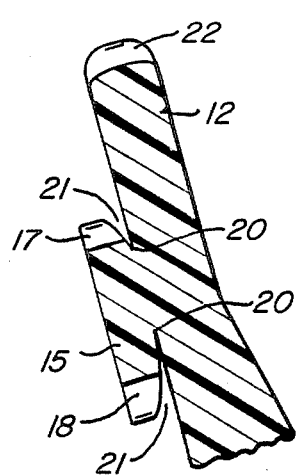
FIG._5A.
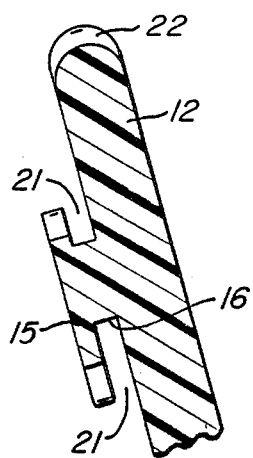
FIG._5B.
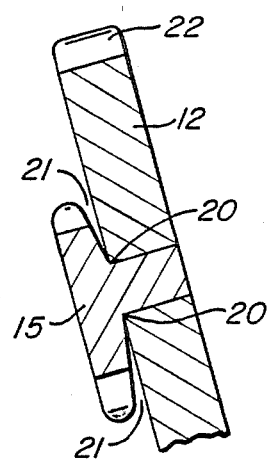
FIG._5C.
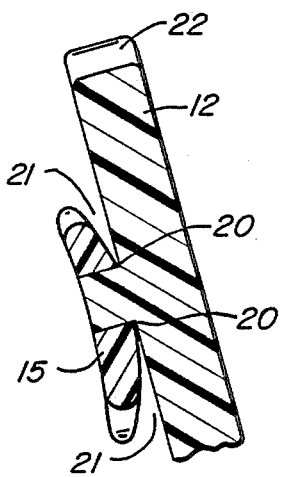
FIG._5D.
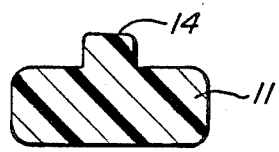
FIG._6.
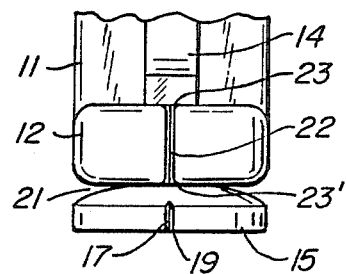
FIG._7.
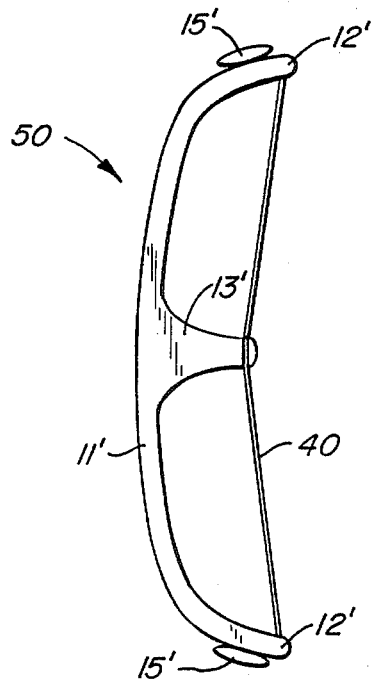
FIG._8.

DENTAL FLOSS HOLDER

BACKGROUND OF THE INVENTION

1. Field of the Invention

This invention relates to oral hygiene equipment, and more specifically to an improved dental flossing device.

2. Cross-Reference to Related Applications

This device is the subject of my design patent application, Ser. No. 06/765804, filed on 8/15/85, entitled DENTAL FLOSS HOLDER.

3. Description of the Prior Art

The dental profession has long recognized the benefits of regular use of dental floss in home dental care programs. Moreover, increasing public knowledge and concern about dental plaque build-up has made flossing a more routine and significant ritual in many households. Heretofore, people have either chosen one of many dental floss holding devices that have been previously known, or they hold and manuever the dental floss with their fingers. The latter procedure often involves wrapping the dental floss around the fingers, sometimes resulting in pain as flossing proceeds; the method of holding and manipulating dental floss with the fingers is also wasteful of flossing material, and is somewhat difficult, the degree of difficulty in part depending upon relative size of fingers and mouth, dexterity, and patience.

Various dental floss holders have been developed to facilitate holding and tensioning the dental floss, and to facilitate the urging of dental floss between the teeth. Some of the prior art dental floss holders necessitate that the manufacturer fabricate and assemble several differently shaped pieces, often resulting in a relatively high-cost device. Few such devices are commonly available in the marketplace at present, in spite of the fact that some of these devices theoretically use floss efficiently, and may have other advantages as well.

Other dental floss holders do not use commonly available dental floss material. These devices sometimes make efficient use of floss, but the floss is usually expensive and hard to find vis-a-vis that commonly available in drug stores.

In the prior art, dental floss holders of disposable design are disclosed. Some are of simple design, but are sometimes marginally effective in maneuverability and/or in maintaining tension when cleaning very many surfaces. Some lack the durability to clean many surfaces, and are costly over the long run if flossing is to be done between all teeth on a daily basis; reusable dental floss holders utilizing commonly available dental floss are often more cost effective.

Of the currently more popular reusable dental floss holders which are of low-cost construction, and which use commonly available dental floss, most have a pair of spaced arms at the end of a supporting handle. A length of dental floss is strung between the ends of the spaced arms which have floss-receiving notches at their terminal ends. The ends of the dental floss are secured in some fashion or another, generally either by winding around a button/protrusion on the handle, or pulling the ends of the dental floss into inwardly tapered notches of frictional securing slots on the handle. These dental floss holders have had only limited success commercially for any number of reasons, often including inadequate securing and/or tensioning of the dental floss and/or a design not easily maneuvered in the back of the mouth, and/or a design wasteful of dental floss, and/or a design with too much bulk and discomfort in use. Among designs which may be wasteful of dental floss are those with only a short span (typically 1.5 to 2.0 cm), of taut dental floss between the spaced arms of a strung system; this usable length of taut dental floss often comprises less than 10% of the total length of dental floss necessary to string and secure the dental floss on the holder. Such designs, with 1.5 to 2.0 cm or so of usable dental floss between the spaced arms, are also often among those designs considered difficult to maneuver—particularly in breaking through tight interproximal contacts. Such a short span of usable dental floss generally precludes adequate performance of a gentle "sawing" motion, and the "brute force" pressure therefore applied to break through these tight contacts sometimes results in cutting the gums, or in losing tension in the dental floss, or in fraying or breaking the dental floss.

In some of the prior art dental floss holders, an already short useable length of taut dental floss is, in effect, further shortened in use due to sometimes inadequate distances, perpendicularly, between a locus of points along the span of taut dental floss and the nearest surface of the supporting member or frame. In such designs, a back-and-forth sawing motion to the gumline between elongated teeth may be possibly only over a limited portion of the short span of taut dental floss, because of significant interference from the supporting member of frame. Other parts of the frame of bulky and/or awkwardly shaped dental floss holders still further limit maneuverability of some devices in the mouth, particularly the ability to perform a relatively long back-and-forth motion between all teeth. The result is that the central portions of the usable length of taut dental floss tend to get more use, and it often frays or breaks quickly in such designs.

Some prior art dental floss holders which use commonly available dental floss material require tie-down, knotting, loop-making, or other special treatment of one of both of the dental floss ends. Such dental floss holders are not commonly available in the marketplace at present.

SUMMARY OF THE INVENTION

1. Objects of the Invention

It is an object of the present invention to provide a dental floss holder of reduced bulk, streamlined for easy insertion and manipulation in the mouth.

An additional object is to provide a dental floss holder which uses commonly available dental floss material, without the need for tying any knots or loops to secure the dental floss to the dental floss holder. Thus, floss material can be purchased easily and economically, and restringing the dental floss holder with floss material will be quick and easy to do.

An object is to provide a reusable dental floss holder which may be inexpensively mass produced.

An object is to provide a dental floss holder which, when strung and the floss ends secured, is capable of presenting in taut condition between spaced arms up to 30% or more of the total length of dental floss required for stringing the floss holder. Another object is to provide a dental floss holder which can be strung with a relatively small total length of dental floss as compared to the length of dental floss generally recommended for flossing when using the method of wrapping the floss around the fingers. One advantage of these features is that there will be more efficient use of dental floss material.

Another object is to provide a dental floss holder wherein the length of taut dental floss between the spaced arms of the device shall be sufficient to permit a long back-and-forth sawing stroke between the spaced arms; moreover, the distances, perpendicularly, from a locus of points along the length of taut dental floss to the nearest surface of the supporting member or frame shall also be sufficient to permit a back-and-forth stroke to the gumline between elongated teeth without significant interference from the supporting member or frame. Another object is to provide a dental floss holder that permits such long back-and-forth strokes and simultaneously maintains a low profile at various angles while in the mouth, and while going in and out of the mouth. The ability to apply gentle back-and-forth strokes of sufficient length, without discomfort or significant interference from the supporting frame, will facilitate sawing through tight interproximal contacts—with reduced probability that the user will resort to thrusts so vigorous that the dental floss may break or fray, or that a sudden, less restrained breakthrough will cause injury to the gums.

A further object is to provide a dental floss holder which has an improved, uncomplicated system for tensioning and more positively fastening the dental floss on the device. The buttons/protrusions that form a part of the dental floss fastening system will not interfere with operation of the device, and will not cause discomfort to the user. Moreover, after winding the second end of the dental floss around the last button/protrusion, the dental floss end shall be further secured to prevent the dental floss from unwinding or loosening.

2. Brief Description of the Invention

To the accomplishment of the above and related objects, this invention may be embodied in the form by a dental floss holder which includes two flexible spaced arms at the opposing ends of a comparatively inflexible, elongate supporting member, and a third, inflexible spaced arm supported by the elongate supporting member, between the flexible spaced arms. A single length of dental floss is first fastened at one flexible spaced arm, then wound around a circumferential notch in the inflexible spaced arm, and finally fastened at the opposing flexible spaced arm. Components of the dental floss fastening system shall be positioned close enough to the terminal ends of the flexible spaced arms so as not to be wasteful of dental floss, and so as to minimize the potential for slack in the length of strung dental floss; further, each of the two fastening systems will include at least one button/protrusion around which the dental floss is wound, as well as one or more frictional securing slots. The dental floss holder, when strung, will provide two relatively long lengths of tensioned dental floss in tandem; and the dental floss holder can easily be held at either end, between a thumb and finger, while the opposing end is placed at least partially into the mouth of the user. Further characteristics, capabilities, and advantages of my invention will become apparent from a consideration of the drawings and ensuing description thereof. Attention is called to the fact that the forms of the invention in the accompanying drawings are only illustrative of a preferred embodiment and four modifications thereof.

BRIEF DESCRIPTION OF THE DRAWINGS

FIG. 1 is a perspective view of a dental floss holder according to a preferred embodiment of my invention.

FIG. 2 is a top view thereof;

FIG. 3 is a side view thereof;

FIG. 4 is an end view thereof;

FIG. 5 is an enlarged, sectional view (taken through Section 5.5 of FIG. 4) showing the preferred embodiment (FIG. 5A) of an oblong button/protrusion with its frictional securing slots, as well as three examples of alternative button/protrusion embodiments (FIGS. 5B, 5C, and 5D);

FIG. 6 is a sectional taken along lines 6—6 of FIG. 2.

FIG. 7 is a fragmentary enlarged view looking down the terminal end of a flexible spaced arm and showing a frictional securing slot and floss receiving notches in the terminal end of the flexible spaced arm;

FIG. 8 is a side view of another embodiment of the device of the invention.

DESCRIPTION OF THE PREFERRED EMBODIMENT

Referring to FIGS. 1-4, there is illustrated a dental floss holder generally designated by reference numeral 10, and comprising a comparatively inflexible elongate supporting member 11 and two flexible spaced arms 12 at the opposing ends of inflexible elongate supporting member 11; between the flexible spaced arms 12 is situated inflexible spaced arm 13. These pieces are integrally formed as a unit, preferably from molded plastic which is easily and economically formed, with rounded and smoothed edges. These pieces are thin enough so that flexible spaced arms 12 can be flexed toward the inflexible spaced arm 13, but still thick enough for the flexible spaced arms 12 to resist breakage in use, and for the inflexible elongate supporting member 11, reinforced in this embodiment by an integral rib 14, to remain comparatively unyielding during use. Integral reinforcing rib 14 extends only part way up flexible spaced arms 12, into which the integral reinforcing rib 14 tapers and disappears. In the preferred embodiment illustrated, the centerline of a given flexible spaced arm 12, except in the area where it joins inflexible elongate supporting member 11, is virtually a straight line when not forced to yield toward the inflexible spaced arm 13. Said straight line portion of the centerline of a given flexible spaced arm 12, if imaginarily extended to intersect the straight line portion of the centerline of the inflexible elongate supporting member 11, would form an angle with the latter centerline exceeding 90°. When said flexible spaced arm 12 is flexed or forced to yield toward the inflexible spaced arm 13, its centerline is no longer straight, but forms an arcuate contour.

FIGS. 1, 3 and 4 show buttons/protrusions 15 symmetrically placed near the terminal ends of flexible spaced arms 12. FIGS. 5A-5D show a button/protrusion 15 in enlarged sectional view, the first, FIG. 5A, being that of the preferred embodiment, and FIGS. 5B, 5C and 5D being examples of alternative embodiments which will be described subsequently. The small circular base 16 in the preferred embodiment of the button/protrusions 15 is best shown in FIG. 4. As shown in FIGS. 4 and 5A, the preferred embodiment, buttons/protrusions 15 are oblong in shape and are integrally formed as a unit with the flexible spaced arms 12, to make it easier to reduce bulk and profile, and to obviate the necessity for costly assembly operations. The oblong buttons/protrusions 15 are thick enough to enable rounding and smoothing of all surfaces and edges which may make contact with any portion of the body, and thick enough also to be very strong so that they resist breaking. However, the oblong buttons/protrusions 15 must not be so thick or large as to be uncomfortable in the mouth.

The oblong buttons/protrusions 15 have frictional securing slots 17 and 18, best shown in FIGS. 4 and 5A, at opposite ends of the oblong buttons/protrusions 15. Referring to FIG. 4, because the lengths of the oblong buttons/protrusions 15 are not centered on their respective circular bases 16, frictional securing slots 17 are not as deep as frictional securing slots 18. The entrances to the frictional securing slots 17 and 18 are relatively wide, floss receiving notches 19 and $19^1$, which immediately reduce in width to form narrow frictional securing slots 17 and 18. As can be seen in the enlarged view of the preferred embodiment, FIG. 5A, the oblong buttons/protrusions 15, together with the flexible spaced arms 12, form circumferential frictional securing slots 20, that have relatively wide and rounded circumferential floss receiving notches 21. As best shown in the enlarged view of FIG. 7, the terminal ends of flexible spaced arms 12 have frictional securing slots 22, the entrances to which are relatively wide and rounded floss receiving notches 23 and $23^1$ situated on opposite sides, at the terminal ends, of flexible spaced arms 12.

Turning again to FIGS. 1 and 3, the inflexible spaced arm 13 has, near its terminal end, a circumferential floss receiving notch 24.

To place the dental floss holder in operation, the user first severs a length of commonly available dental floss material from a roll of same (not shown). One end of the dental floss is held, temporarily, by the thumb against the lower portion of either one of the flexible spaced arms 12, below the oblong buttons/protrusions 15. The same thumb, together with a finger against the other side of flexible spaced arm 12, grips the dental floss holder. The free end of the dental floss is taken in the other hand, wound two or three times around oblong button/protrusion 15, the floss first dropping into circumferential floss receiving notch 21, and being pulled tight into circumferential frictional securing slot 20. The dental floss is then pulled upward through floss receiving notch $19^1$ and into frictional securing slot 18. The hand gripping the dental floss holder is then repositioned to grip, between thumb and finger, the dental floss holder between the outside surfaces of flexible spaced arms 12. Pressure applied by squeezing the flexible spaced arms 12 inward causes them to form arcuate contours as they yield toward inflexible spaced arm 13.

Now keeping the dental floss taut with the other hand, it is pulled through floss receiving notch $23^1$, to the bottom of frictional securing slot 22, wrapped once around floss receiving notch 24, then pulled through the floss receiving notch 23 of the opposite flexible spaced arm 12, and to the bottom of its frictional securing slot 22; still applying pressure against the flexible spaced arms 12 and keeping the dental floss taut, it is wound a desired number of times through circumferential floss receiving notch 21, each time pulling the dental floss tightly into frictional securing slot 20. Finally, the loose end of the dental floss is secured by pulling it first through floss receiving notch 19, into frictional securing slot 17, then through floss receiving notch $19^1$ and into frictional securing slot 18. FIG. 4 illustrates how the dental floss looks when viewing the dental floss holder at the end, at which stringing has been completed. The pressure is then released against flexible spaced arms 12, which will cause them to move away from each other if the dental floss, already tightly drawn and secured, should loosen slightly while the dental floss holder is being vigorously used.

As shown in FIG. 1, between each flexible spaced arm 12 and the inflexible spaced arm 13, there is now a relatively long length of tensioned dental floss 40. Each length of dental floss may be used in turn to clean between the teeth; the user will first grip the dental floss holder at one end, between a thumb and finger, and use the length of dental floss stretching from inflexible spaced arm 13 to the opposite end; when the other, still fresh, length of dental floss is desired, the user grips the dental floss holder at the opposite end. The absence of a bulky handle, and the low profile of the strung dental floss holder at various angles in the mouth are among the factors enabling the device to be easily manipulated within the mouth, with minimal obstruction of view and/or discomfort. One of the important features of the design is the ability of the user to gently work down through an interproximal contact, or to break through tight/rough contact areas in which the dental floss has become stuck, using a relatively long back-and-forth stroke, manipulating the device as if it were a miniature violin bow. The same long back-and-forth strokes enable efficient cleaning to the gumline of elongated teeth, not only because of the relatively long lengths of usable dental floss, but also because the design of the device enables long strokes all the way to the gumline, without significant interference from the dental floss supporting member or frame.

To string the dental floss holder of the present invention takes a much smaller total length of dental floss material than the 45 centimeter length commonly recommended when a dental floss user wraps each end of the dental floss around the fingers. Also, it can be seen, compared to those dental floss holders in the prior art which are designed to use commonly available dental floss without tying knots or loops, that the present invention uses dental floss efficiently. This efficient use of dental floss is attributable in part to the close proximity of the dental floss fastening system to the terminal ends of the flexible spaced arms 12, and also to other design features of the present invention which allow 30% or more of the total length of dental floss necessary to string the device to be available in a taut condition between spaced arms, without tying knots. In a model of the preferred embodiment, no more than a 23 centimeter total length of dental floss is necessary to string the device, about 7.5 centimeters of which is taut and usable dental floss between spaced arms.

Referring to the above detail concerning the placing of the dental floss holder in operation, it is seen that, at the end of the dental floss holder where the stringing of dental floss is begun, frictional securing slot 17 is not used. This is a matter of user choice, as the dental floss stringing could, for example, begin by holding the dental floss end near the terminal end of flexible spaced arm 12, then pulling the dental floss through floss receiving notches 19 and $19^1$, and into frictional securing slots 17 and 18, respectively, before beginning to wind around oblong button/protrusion 15 through circumferential floss receiving notch 21. However, the user will find such alternative initial steps generally unnecessary, because winding the dental floss a second or a third time around oblong button/protrusion 15 has already wedged the end of the dental floss into circumferential frictional securing slot 20. However, as the stringing operation of the dental floss holder is completed at the opposite oblong button/protrusion 15, the other end of the dental floss has not been securely wedged after winding it around oblong button/protrusion 15. There is, therefore, a more substantial need for frictional securing slots 17 and 18 at the end at which stringing is completed. Because, in the preferred embodiment, the user may start the stringing operation at either one of the flexible spaced arms 12 without thinking, frictional securing notch 17 is not omitted from one end of the design.

In the examples of alternative button/protrusion embodiments shown in FIGS. 5B, 5C, and 5D, the tooling necessary to mass produce the dental floss holder is less expensive to construct than the tooling required for the preferred embodiment, shown in FIG. 5A. Referring to the first alternative, FIG. 5B, this embodiment omits the circumferential frictional securing slots 20; the floss receiving notches 21 receive the dental floss, but do not frictionally secure the dental floss; however, other frictional securing slots of the preferred embodiment are retained. In the second alternative embodiment shown in FIG. 5C, the buttons/protrusions 15 are manufactured as separate elements with shafts protruding from the base; these buttons/protrusions may be easily assembled to the flexible spaced arms 12 which have been manufactured with holes to receive the shaft. In yet a third alternative embodiment of the buttons/protrusions shown in FIG. 5D, integral shafts protruding from the surface of the flexible spaced arms 12, are designed to receive buttons with holes; the buttons with holes are manufactured as separate elements.

In the embodiment of FIG. 8, the dental floss holder 50 has parts which are operationally the same as the parts of dental floss holder 10, except that the function of the integral reinforcing rib 14 has been replaced with an inflexible elongate supporting member $11^1$ with a greater cross section than that of the flexible spaced arms $12^1$. Physically, another difference is that the centerlines of flexible spaced arms $12^1$ form an arcuate contour throughout their length, even when not forced to yield toward the inflexible spaced arm $13^1$. Also, the comparatively inflexible elongate supporting member $11^1$ forms an arcuate contour, but of different curvature from the arcuate contours of the flexible spaced arms $12^1$. The dental floss holder thus takes on even more of a resemblance to a miniature archer's bow, but it differs from such a bow, in particular, in that the large central section of the frame of an archer's bow is usually designed to flex, while that of the dental floss holder 50 is not. The distances perpendicularly from the strung dental floss to the supporting frame are more nearly constant in the embodiment of dental floss holder 50 than those of dental floss holder 10. Some users may prefer to manipulate the modified dental floss holder 50 rather than dental floss holder 10.

While the above descriptions contain many specifications, these should not be construed as limitations on the scope of the invention, but, rather, as an exemplification of one preferred embodiment and four modifications thereof. Many other variations are possible; for example, a dental floss fastening system on one flexible spaced arm 12 may omit frictional securing slot 17 together with floss receiving notches 19, but retain the dental floss fastening system of the preferred embodiment on the opposite flexible spaced arm 12; as has been noted, adequately securing the starting end of the dental floss is less difficult than securing the opposite end of the dental floss. Another example is to mold into the flexible spaced arms 12 a slightly enlarged section in which additional frictional securing slots are molded without appreciably weakening the flexible spaced arms 12; or such frictional securing slots might replace frictional securing slots 17 and 18. Another example would be to add a second button/protrusion to the same flexible spaced arm 12 at which stringing of the dental floss holder is completed, thereby providing still more positive means of securing that end of the dental floss. Still another example would be to change the length and/or shape of the button/protrusion 15 of the preferred embodiment, and to lengthen and/or change the position of the frictional securing slots 17 and 18. Another example would be to move the location of the buttons/protrusions 15 closer to the terminal ends of flexible spaced arms 12, providing an even more efficient use of dental floss. Another example is to move the position of the inflexible spaced arm 13 to another location along the inflexible elongate supporting member 11, thereby causing a strung dental floss holder to present one longer length of taut and usable dental floss and one shorter length of taut and usable dental floss.

Accordingly, the scope of the invention should not be determined by the embodiments illustrated, but by the appended claims and their legal equivalents.

I claim:

1. A dental floss holder for receiving a single length of commonly available dental floss and retaining said dental floss in a taut condition without tying knots or loops, and comprising in combination:
    a. A comparatively inflexible elongate member supporting two flexible spaced arms at opposing ends, and supporting a circumferentially notched inflexible spaced arm lying between and extending in the same direction as said flexible spaced arms to provide two spans, one between each flexible arm and said inflexible arm, each defining a span for a taut and usable length of said dental floss, there being two said taut and usable lengths of dental floss in tandem when said dental floss holder has been strung for use,
        (1) said flexible spaced arms and inflexible spaced arm positioned apart sufficiently to allow each of said taut and usable lengths of dental floss to easily span the largest molars, with room for a back-and-forth sawing motion,
        (2) said dental floss holder being grasped between thumb and finger at one end while said taut and usable length of dental floss at the opposite end is positioned for use in the mouth;
    b. A means for fastening the ends of said dental floss comprising, said flexible spaced arms having
        (1) at least one frictional securing slot at the terminal end of said flexible spaced arms for engaging said dental floss,
        (2) at least one button near the terminal end of each of said flexible spaced arm, around which said dental floss is wound, each said button itself forming, together with said flexible spaced arm, a frictional circumferential securing slot,
        (3) each said button having still further a frictional securing slot formed through the center thereof.

2. The dental floss holder of claim 1 wherein said inflexible elongate member and said flexible spaced arms together form a supporting frame for said taut and usable lengths of dental floss in tandem, said supporting frame when strung with said dental floss is bow-shaped with turned-up ends.

3. The dental floss holder of claim 2 wherein said supporting frame is integrally formed of plastic.

4. A dental floss holder, for receiving a single length of commonly available dental floss and retaining said dental floss in a taut condition, without tying knots or loops, and comprising in combination:

- a. A comparatively inflexible elongate member supporting two flexible spaced arms at opposing ends, and supporting a circumferentially notched inflexible spaced arm lying between and extending in the same direction as said flexible spaced arms, said inflexible elongate member and said spaced arms together forming both a supporting frame for supporting two taut and usable lengths of said dental floss in tandem, as well as a means for holding, between finger and thumb, said dental floss when in use,
  (1) said supporting frame being of low bulk and having a generally elongate shape, either end of which may be inserted in the mouth and used while being held at the other end,
  (2) said supporting frame having relatively low profile at various angles while in the mouth and while going in and out of the mouth;
  (3) said supporting frame having been formed to provide a distance between the terminal end of either said flexible spaced arm and the nearest edge of the circumferential notch in said inflexible spaced arm sufficient to easily span the buccal and lingual surfaces of the largest molar, with ample space remaining for a back-and-forth sawing motion between teeth,
  (4) said supporting frame having been formed so that the range of distances perpendicularly, from a locus of points along each said taut and usable length of dental floss to the nearest surface of said supporting frame, is adequate to allow each said taut and usable length of dental floss to be manipulated in long back-and-forth sawing motions to the gumline between elongated teeth, without significant interference from said supporting frame;
- b. A fastening means for each end of said dental floss, said fastening means being physically near the terminal end of each said flexible spaced arm, and consisting of at least one button around which said dental floss is wound, this in combination with said at least one button having at least one frictional securing slot to engage said dental floss,
- c. A length of said dental floss strung from one of said fastening means on one of said flexible spaced arms, then around the circumferential notch of said inflexible spaced arm, thence to said fastening means on the other of said flexible spaced arms, thereby forming the two said taut and usable lengths of dental floss in tandem, one between said one of said flexible spaced arms and said inflexible spaced arm, and the second between said other of said flexible spaced arms and said inflexible spaced arm, said dental floss to have been strung tightly while applying pressure against the outside surfaces of said flexible spaced arms.

5. The dental floss holder of claim 4 wherein said supporting frame when strung with said dental floss is bow-shaped with turned-up ends.

6. The dental floss holder of claim 5 wherein said supporting frame is integrally formed of plastic.

7. The dental floss holder of claim 4 wherein said taut and usable lengths of dental loss in tandem have a combined length that is 30 percent or more of the total length of said dental floss necessary to securely string said dental floss holder.

* * * * *